United States Patent [19]

Mihelich

[11] 4,345,984
[45] Aug. 24, 1982

[54] NOVEL PROSTAGLANDIN ANALOGUES AND PROCESS FOR MAKING SAME

[75] Inventor: Edward D. Mihelich, Fairfield, Ohio

[73] Assignee: The Procter & Gamble Company, Cincinnati, Ohio

[21] Appl. No.: 239,765

[22] Filed: Mar. 2, 1981

[51] Int. Cl.$^3$ .......................................... C07C 301/16
[52] U.S. Cl. ............................... 204/162 R; 560/121; 562/503; 568/591; 424/305; 424/317; 549/533
[58] Field of Search ................ 260/348.33; 204/162 R

[56] References Cited

U.S. PATENT DOCUMENTS

| | | | |
|---|---|---|---|
| 3,259,638 | 7/1966 | Allison | 260/348.5 |
| 4,021,369 | 5/1977 | Lyons | 252/425 |
| 4,175,201 | 11/1979 | Fried | 560/17 |
| 4,180,672 | 12/1979 | Kurozumi et al. | 560/15 |

OTHER PUBLICATIONS

Isaacs, Reactive Intermediates in Organic Chemistry, pp. 471-474 (1974).
Coxon et al., Organic Photochemistry, pp. 154-163 (1974).
Corey, "Studies on the Total Synthesis of Prostaglandins", Ann. N.Y., Acad. Sci., 180, (1971) 24.
Fried, et al., "Synthesis and Biological Activity of Prostaglandins and Prostaglandin Antagonists", Ann. N.Y., Acad. Sci., 180, (1971) 38.
Fried et al., "Synthesis of (+) and (−)-7-Oxaprostaglandin F$_{1\alpha}$ and Their Epimers", J. Am. Chem. Soc. 93, (1971) 5594.
Fried, et al., "Synthesis of (+)-7-oxaprostaglandin F$_{1\alpha}$", Chem. Comm., (1968) 634.
Fried, et al., "Regiospecific Epoxide Opening with Acetylenic Alanes", J. Am. Chem. Soc., 94, (1972) 4343.
Kaneda, et al., "Direct Epoxy Alcohol Synthesis from Cyclic Olefins Using O$_2$ and VO(acac)$_2$-AIBN Catalyst System", J. Org. Chem. 45, (1980) 3004.
Allison, et al., "Preparation and Chemistry of Epoxy Alcohols", Ind. Eng. Chem., (Prod. Res. and Dev.) 5, (1966) 166.
Lyons, "The Stereoselective Oxidation of Cyclohexene to cis-1,2-Epoxy cyclohexane-3-ol in the Presence of C$_5$H$_5$V(CO)$_4$", Tetrahedron Lett., 32, (1974) 2737.
Mercier, et al., "Comportement d'Hydroperoxydes Allyliques a Longue Chaine en Présence de Complexes de Certains Metaux de Transition", Chem. Phys. Lipids, 12, (1974) 232.
Kopecky, et al., "Reactivity in Photosensitized Olefin Oxidations", Can. J. Chem., 43, (1965) 2265.

*Primary Examiner*—Robert Gerstl
*Attorney, Agent, or Firm*—Jack D. Schaeffer; Steven J. Goldstein; Richard C. Witte

[57] ABSTRACT

A novel process for the oxidation of olefins to the corresponding alpha-epoxy alcohols which can be incorporated in the total synthesis of members of a novel class of prostaglandin analogues.

Olefins are reacted with singlet oxygen in the presence of a group IVB, VB or VIB transition metal catalyst, excluding chromium. The reaction is fast and highly selective to the alpha-epoxy alcohol. When cyclopentene is oxidized in the process of the invention, high yields of cis 2,3-epoxy-cyclopentan-1-ol are obtained. The latter compound is used as a starting material in the synthesis of prostaglandin analogues. The prostanoids of the invention are characterized by an oxa group replacing the methylene group at the 7-position, and the absence of a hydroxyl or other substituent at the 11-position.

Members of this class of prostanoids show important cytoprotective properties in animal tests.

8 Claims, No Drawings

NOVEL PROSTAGLANDIN ANALOGUES AND PROCESS FOR MAKING SAME

TECHNICAL FIELD

This invention relates to a process of making a novel class of prostaglandin-like compounds.

Since the discovery of the naturally occurring prostaglandins and their important biological properties, a tremendous research effort has been devoted to the synthesis of these compounds. Although much progress has been made in the development of synthesis routes for the natural prostaglandins, a major stumbling block remains—the requirement of stereospecific substitution at the positions 8, 9, 11 and 12 (c.f. prostanoic acid, compound (I).

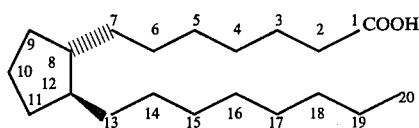

One solution to this problem is the art-disclosed synthesis of the 7-oxa prostaglandin analogues (III) which uses all cis 3,5-dihydroxy-1,2-epoxycyclopentane (II) as a starting material.

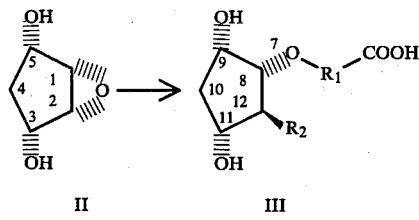

A key feature of this synthesis is the trans opening of the oxirane by nucleophilic attack. Although this synthesis solves the problem of the trans substitution at the 12-position, it creates the new problem of isomer selective synthesis of all cis 3,5-dihydroxy-1,2-epoxycyclopentane. In an attempt to avoid the latter problem, prostaglandin-type compounds (V) have been synthesized from 1,2-epoxycyclopentane (IV). However, this further deviation from

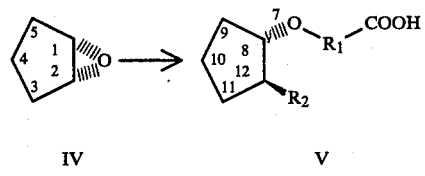

the natural prostaglandin structure (elimination of the hydroxyl groups at the 9 and 11 positions) results in an erratic biological activity of the compounds thus obtained; some of them act as prostaglandin agonists in one test, and as antagonists in another.

No attempt has been made thus far to use cis-2,3-epoxycyclopentan-1-ol (VI)

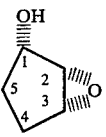

as a starting material in the synthesis of prostaglandin analogues. This is not surprising, as no attractive synthesis route for (VI) has been available thus far.

Normally, (VI) is synthesized by reacting cyclopenten-3-ol, a relatively expensive starting material, with t-butyl hydroperoxide in the presence of a vanadium catalyst. Typically a 45% isolated yield is obtained after 2 days. The reaction time is less (about 1 day) if the t-butyl hydroxperoxide is replaced with a peracid, but then a significant amount of the trans isomer is formed (cis:trans ratio about 4:1).

Even if cis-2,3-epoxycyclopentan-1-ol were readily available, it would not be expected to be a suitable starting material for the synthesis of prostaglandin-like materials. Because of the asymmetry of the molecule, the oxirane bond opening would be expected to result in two regio-isomers, of which only one would be suitable for further synthesis; and the resulting prostanoid would lack the hydroxyl group at the 11-position which would make it, in view of the state of the art, doubtful whether biological activity of any significance would be possessed by this class of prostanoids.

By the present invention it has been discovered that olefins can quite readily be converted to the corresponding alpha-epoxy alcohols when they are reacted with singlet oxygen in the presence of a suitable oxidation catalyst. The reaction is fast, gives high yields, has a high selectivity towards the epoxy alcohol, and uses an inexpensive starting material.

It has further been discovered that when cyclopentene is subjected to the process of this invention, cis-2,3-epoxycyclopentan-1-ol is obtained in high yield. It has surprisingly been found that when this compound is, after suitable protection of the hydroxyl group, subjected to a nucleophilic attack on the oxirane, the trans opening of the epoxide is regio-selective. This makes this compound particularly suitable for the synthesis of a novel class of prostanoids. Members of this class unexpectedly show important cytoprotective activity.

BACKGROUND ART

Different syntheses of prostaglandins are reviewed by Corey, Ann. N.Y. Acad. Sci., 180 (1971) 24. The 7-oxa-prostaglandins are discussed by Fried, et al., Ann. N.Y. Acad. Sci., 180 (1971) 38. Other publications related to the synthesis of 7-oxa-prostaglandins include: Fried, et al., J. Am. Chem. Soc., 93 (1971) 5594; Fried, et al., Chem. Comm. (1968) 634. The 7-thia prostanoids are disclosed in U.S. Pat. No. 4,175,201 granted Nov. 20, 1979 to Fried, and U.S. Pat. No. 4,180,672 granted Dec. 25, 1979 to Kurozumi, et al.

The effect of a free hydroxyl group on the regio-specificity of the epoxide opening is discussed in Fried, et al., J. Am. Chem. Soc., 94 (1972) 4343.

The catalytic oxidation of olefins to alpha-epoxy alcohols is dealt with by Kaneda, et al., J. Org. Chem. 45 (1980) 3004; Allison, et al., Ind. and Eng. Chem. (Prod. Res. and Dev.) 5 (1966) 166; Lyons, Tetrahedron Lett. 32 (1974) 2737; U.S. Pat. No. 3,259,638, granted July 5, 1966 to Allison. A bimetallic catalyst for this reaction is disclosed in U.S. Pat. No. 4,021,369, granted May 3, 1977 to Lyons.

The preparation of alpha-epoxy alcohols via catalytic rearrangement of hydroperoxides is discussed by Mercier, et al., Chem. Phys. Lipids 12 (1974) 232. The use of singlet oxygen in the reaction of olefins to hydroperoxides is disclosed by Kopecky, et al., Can. J. Chem., 43 (1965) 2265.

Although much effort has been made to improve the process of catalytic oxidation of olefins to alpha-epoxy alcohols, the processes reported in the art suffer from low reaction rates, low yields, and poor selectivities. The rearrangement of hydroperoxides is fast, but requires separate preparation of these peroxides and their isolation. The process of this invention is fast, gives high yields and is highly selective. Moreover, the process herein is especially adaptable to a total synthesis of prostaglandin analogues, using cyclopentene as a starting material.

SUMMARY OF THE INVENTION

In one of its aspects, the present invention is a process for the photo-oxidative conversion of olefins to alpha-epoxy alcohols using a vanadium catalyst.

The present invention also encompasses a process for making prostaglandin analogues using cyclopentene as a relatively inexpensive starting material. The first step in this process is the conversion of cyclopentene to cis-2,3-epoxycyclopentan-1-ol by reacting cyclopentene with singlet oxygen in the presence of a catalytic amount of a catalyst containing a transition metal of group IVB, VB, or VIB of the Periodic Table, excluding chromium. Application of this process to the conversion of other olefins to the corresponding alpha-epoxy alcohols is also within the scope of this invention.

The next step is a nucleophilic attack on the oxirane bond with an alkynylalene reagent, resulting in a regioselective trans opening. Prior to this reaction, the hydroxyl group is protected against nucleophilic attack with a suitable protecting group. In the next step, the substituent at the 8-position is attached via a Williamson synthesis. Deprotection and tailoring of the oxidation states at the 9-position and in the substituent chains leads to the desired prostaglandin analogues, as described more fully hereinafter.

Finally, the present invention encompasses a new class of prostaglandin analogues which are characterized by an oxygen atom replacing the methylene group at the 7-position, and the absence of a hydroxyl substituent at the 11-position. Members of this class have been found to possess cytroprotective properties which make them useful for the prevention and treatment of gastric ulcers.

DETAILED DESCRIPTION OF THE INVENTION

By "olefin" herein is meant an aliphatic hydrocarbon having at least one double bond and at least one allylic hydrogen. By "mono-olefin" herein is meant an olefin with one double bond.

By "corresponding alpha epoxy alcohol" herein is meant that when the olefin starting material has its double bond between the carbon atoms m and m+1, the alpha-epoxy alcohol formed is the m-hydroxy-(m+1), (m+2)-epoxy compound or the (m+1)-hydroxy-(m−1), m epoxy compound.

By "heterogeneous catalyst" herein is meant a catalyst which is in the solid state and is not soluble in the reaction mixture.

By "homogeneous catalyst" herein is meant a catalyst which is soluble in the reaction mixture.

By "acac" herein is meant acetylacetonate.

By "singlet oxygen" herein is meant oxygen molecules in the lowest excited electronic state that has spin multiplicity of one, generally denoted as the $^1\Delta g$ state.

By "photo-sensitizer" herein is meant an organic compound which can be excited to the triplet state by adsorption of visible light.

By "catalytic amount" herein is meant an amount significantly less than a stoichiometric amount which is sufficient to act as a catalyst in the reaction.

By "prostaglandin analogue" herein is meant a compound which is structurally similar to the naturally occurring prostaglandins.

By "7-oxa-11-deoxy prostaglandin analogue" herein is meant a compound structurally similar to the natural prostaglandins of the E-series or F-series, characterized by an oxa group replacing the methylene group at the 7-position, and by the absence of a hydroxyl substituent at the 11-position.

By "suitable protecting group" herein is meant any base stable protecting group for alcohols. Examples thereof are ethers, in particular methoxymethyl, t-butyl, benzyl, dimethyl-t-butylsilyl and methylthiomethyl ether. Protection of alcoholic hydroxyl groups is discussed by Reese, in "Protective Groups in Organic Chemistry", McOmie, editor, Plenum Press (1973) p. 95 et seq., which is incorporated herein by reference. In case one of the hydoxyl groups is protected with a dimethyl-t-butylsilyl group, the hydroxyl group can be deprotected selectively by reaction with tetrabutyl ammonium fluoride. The procedure is described by E. J. Corey, et al., *J. Am. Chem. Soc.*, 94, 6190 (1972), incorporated herein by reference.

By "alkynyl alane reagent" herein is meant the dialkylalkynylaluminum compound formed by reaction of dialkylaluminum chloride with a lithio-1alkyne.

Percentages herein are mole percentages, unless otherwise indicated.

The first aspect of this invention is a process for converting olefins to the corresponding alpha-epoxy alcohols comprising reacting an olefin with singlet oxygen and converting the reaction product to an alpha-epoxy alcohol by in situ rearrangement in the presence of a catalytic amount of a heterogeneous or homogeneous catalyst containing a transition metal of group IVB, VB or VIB of the Periodic Table, excluding chromium. When cyclopentene is subjected to this oxidation reaction, the major product is cis 2,3-epoxycyclopentan-1-ol.

The present oxidation process has general applicability to all olefins capable of reaction with singlet oxygen, that is, alkyl substituted olefins having at least one allylic hydrogen. Preferred herein are dialky substituted olefins. The double bond may be acyclic, as in alkenes, or semi-cyclic, as in sabinene and beta-pinene, or endocyclic, as in the cycloalkenes. Olefins having functional substituents, such as halogens, carboxyl radicals, etc., at the alpha-position with respect to the double bond are less suitable for the oxidation reaction disclosed herein, and fall outside the scope of this invention.

A detailed discussion of olefin reactions with singlet oxygen is given by Gollnick, et al., in "Singlet Oxygen", Wasserman and Murray, editors, Academic Press (1979), incorporated herein by reference.

Singlet oxygen from any source may be used in the olefin oxidation reaction. Thus, singlet oxygen can be generated by contacting ground-state oxygen with a photo-sensitizer which has been excited by irradiation with visible light, by the reaction of sodium hypochlorite with hydrogen peroxide; by reaction of hydrogen peroxide with bromine in an alkaline medium; by decomposition of the 1:1 adduct of triphenyl phosphite and ozone generated by passage of ozone into a solution of triphenyl phosphite in methylene chloride; by thermal decomposition of epidioxides; or by microwave discharge in a stream of gaseous oxygen. The different methods of generating singlet oxygen are discussed in more detail by Denny, et al., in "Organic Reactions", vol. 20 (W. G. Dauben - editor-in-cheif), published by John Wiley & Sons, p. 133–136, incorporated herein by reference. For purposes of the present invention, singlet oxygen is preferably generated by contacting ground-state molecular oxygen with a suitable photosensitizer which is activated by irradiation with visible light.

Suitable sensitizers are those organic compounds which have a large molar absorptivity in the visible part of the electromagnetic spectrum, a high quantum yield of triplet formation, a long triplet lifetime, a low tendency toward hydrogen abstraction and self-oxidation, and a triplet energy not far above the energy of singlet oxygen to permit efficient energy transfer to oxygen. Many common dyes meet these requirements adequately. Typical classes of dyes that can advantageously be used in the olefin oxidation process of this invention are the xanthenes (rose bengal, erythrosin, eosin, fluorescein), the thiasines (methylene blue), the porphyrins (chlorophyll a and b, hematoporphyrin), the porphins and the phthalocyanines and mixtures thereof. These and other dyes are disclosed in the Denny reference, cited supra, and incorporated herein by reference.

Preferred photo-sensitizers for the present invention are the phthalocyanines and tetraphenylporphin, and most preferred is tetraphenyl porphin.

For optimum efficiency, the amount of photosensitizer should neither be very low nor very high. At very low concentrations the sensitizer may not absorb all the available useful light. At too high a concentration, it absorbs all the useful light within a short distance from its entrance to the solution and depletes oxygen in that region of the reaction vessel. Preferred amounts of sensitizer range from about 0.01% to about 2.5%, more preferably amounts range from about 0.05% to about 1.3%.

Any source of visible light is suitable for the activation of the sensitizer. However, for maximum efficiency, the source should strongly emit light of the wavelength corresponding with the absorptivity maximum of the sensitizer. Thus, a sodium vapor discharge tube is particularly suitable for use in combination with tetraphenyl porphin.

Any catalyst capable of converting the reaction product of the olefin with singlet oxygen, presumably a hydroperoxide, to an alpha-epoxy alcohol is suitable for use in the olefin oxidation reaction of the present invention. Suitable catalysts are those which contain a transition metal of the groups IVB, VB, or VIB of the periodic table. Although both heterogeneous and homogeneous catalyst systems can be used, homogeneous catalysts are preferred for their superior selectivity. Suitable homogeneous catalysts are soluble salts and metallo-organic complexes of transition metals of group IVB, VB, or VIB of the Periodic Table, excluding chromium. Preferred herein are the soluble salts and metallo organic complexes of vanadium and molybdenum. Examples are vanadyl acetylacetonate, molybdenyl acetylacetonate, molybdenum hexacarbonyl, tungsten hexacarbonyl, and vanadium carbonyl. Other examples of suitable catalysts are disclosed by Allison, et al., Ind. & Eng. Chem. (Prod. Res. and Dev.) 5 (1966) 166, incorporated herein by reference.

Preferred catalysts are those containing vanadium or molybdenum; more preferred are those containing vanadium (IV), and most preferred is vanadyl acetylacetonate.

The amount of catalyst should be sufficient to ensure instantaneous conversion of the hydroperoxides. Much higher levels of catalyst may adversely affect the efficiency of the photo-sensitization reaction, as most catalyst systems absorb visible light.

Suitable levels of catalyst range from about 0.1% to about 2.5%. Preferred levels range from 0.7% to 1.3%.

Without limitation by theory, the superior yields of alpha epoxy alcohol obtained with the process of the present invention in comparison with art disclosed processes is believed to be, at least in part, due to the presence of the catalyst at the time the reaction intermediate, the hydroperoxide, is formed. The hydroperoxide is instantaneously converted to the epoxy alcohol by the action of the catalyst. Hence, the concentration of hydroperoxide remains low throughout the reaction period, and side reactions resulting in ketones and alkenols are suppressed.

Although the olefin oxidation reaction of this invention does not require a solvent, better yields are obtained when a solvent is present. Any organic solvent which is miscible with the olefin, and readily dissolves the photo-sensitizer and the catalyst, is suitable. The reaction mixture may contain from about 5% to about 98% of the solvent. Alcohols should not be used, however, as they tend to interact too strongly with the active sites of the catalyst and make it inactive. The reaction mixture should be substantially water-free, as water interacts with the catalyst as well. Examples of suitable solvents are methylene dichloride and toluene.

The olefin oxidiation process of this invention can be used for the conversion of any olefin capable of reaction with singlet oxygen to the corresponding alpha-epoxy alcohol. Examples of suitable olefins are cyclopentene, cis-9-octadecenoic acid esters, cis-4-octene, 2,3-dimethyl-2-butene, alpha-pinene and beta pinene. If the olefin is a cyclic alkene, the reaction is highly selective to the cis epoxy alcohol. Thus, oxidation of cyclopentene yields cis 2,3-epoxycyclopentan-1-ol.

The high reaction rate, the high yield and the selectivity towards the cis configuration makes this reaction useful in a total synthesis of prostaglandin analogues.

The following examples illustrate that with the olefin oxidation process of this invention, alpha epoxy alcohols are obtained in high yields after a reaction time of only several hours.

EXAMPLE I

Cyclopentene was converted to cis-2,3-epoxycyclopentan-1-ol in the following manner.

A solution of cyclopentene (27.25 g, 0.4 m), tetraphenylporphin (0.15 g, 0.061 mole %), vanadium (IV) oxide bis (2,4-pentanedionate) (0.33 g, 0.31 mole %) in 380 ml dry toluene was irradiated with a 400 watt sodium lamp (General Electric LU 400) in an immersion well configuration while cooling with circulating water and continuously purging with oxygen. The solution temperature was maintained at 24° C. and vaporized materials returned to the reaction well by trapping with a cold water condenser. The reaction could be monitored by gas chromatography (gc) or thin layer chromatography on silica gel. After 3 hours, gas phase chromatographic analysis showed >90% conversion and <10% each of cyclopentene oxide, 2-cyclopentenone, and 2-cyclopenten-1-ol by-products. The reaction mixture was stirred for 15 minutes with 1 g triphenylphosphine to destroy any exces hydroperoxide, concentrated, diluted with 200 ml ether, the solid precipitate filtered off and concentrated again. Distillation through a 10 cm Vigreux column gave, after a small forerun, 20.24 g of colorless oil BP59° C. (0.65 mm Hg) which was 99.8% pure by gc analysis and contained 0.2% trans-isomer. The yield was analyzed by gc was 72 mole % of the starting olefin. The isolated yield after distillation was 50.5%. The difference was caused by distillation losses.

This example shows that high yields of cis-2,3-epoxycyclopentan-1-ol can be obtained with the process of this invention after an unusually short reaction time. It also shows the high selectivity to the cis isomer.

TABLE I

Conversion of a number of olefins. The catalyst was vanadyl acetylacetonate. The solvent was toluene, except where otherwise indicated.

| OLEFIN | TIME (hrs) | YIELD[1] (%) | CONVERSION (%) |
|---|---|---|---|
| Methyl oleate | 3.5 | 97.5[2] | >99 |
| cis-4-octene | 5 | 83.4[3] | >95 |
| 2,3-dimethyl[4] 2-butene | 1.5 | 72[5] | >99 |
| cyclopentene | 3 | 50.5[6] | >90 |
| alpha-pinene | 3 | 54[7] | >90 |
| beta-pinene | 6 | 52[8] | >95 |

[1]Isolated yield, defined as mole percentage of olefin starting material
[2]Mixture of methyl-9-hydroxy-10,11-epoxyoctadecanoate and methyl-8,9-epoxy-10-hydroxyoctadecanoate
[3]5,6-epoxyoctan-4-ol
[4]Solvent is dichloromethane
[5]2,3-dimethyl-3,4-epoxybutan-2-ol
[6]2,3-epoxycyclopentan-1-ol, 99.8% cis
[7]6,10-epoxypinan-5-ol
[8]5,6-epoxypinan-10-ol

EXAMPLE II

The process of this invention can be used for the conversion of a broad spectrum of olefins to the corresponding alpha epoxy alcohols. All conversion reactions are characterized by a high conversion, a short reaction time and a high yield of the epoxy alcohol.

Methyl oleate (14.83 g, 0.05 mol) was photooxidized in the manner described in Example I (0.15 g tetraphenylporphin, 0.132 g VO(acac)$_2$). The reaction mixture was concentrated, diluted with 0.2 L ether, and washed with water (2×0.11) and brine (2×0.11). After drying with magnesium sulfate and concentrating, the crude product was chromatographed on silica gel to give the pure epoxy alcohol as a mixture of diastereomers. Isolated yields and reaction conditions are given in Table I.

Alpha and beta pinene were oxidized and purified in the same way. Conditions and results are given in Table I.

Cis-4-octene and 2,3-dimethyl-2-butene were oxidized in the manner described in Example I, and the distilled yields determined. The results are given in Table I. Other olefins capable of reaction with singlet oxygen are oxidized in the same manner. Similar results are obtained.

EXAMPLE III

The cyclopentene oxidation of Example I was repeated with Mo(CO)$_6$, Ti(i-PrO)$_4$ and VO(acac)$_2$ as oxidation catalysts. The reactions were run on 0.4 mole of cyclopentene using methylene dichloride as solvent. The conversions after three hours and the product distributions obtained with the different catalysts are given in Table II.

The best yield of 2,3-epoxycyclopentan-1-ol was obtained with the vanadium catalyst. Both the molybdenum and the titanium catalyzed reactions produced some 2,3-epoxycyclopentan-1-one, whereas very little if any was formed in the vanadium catalyzed reaction. The reactions with V and Mo gave selectively the cis-epoxy alcohol, whereas the Ti catalyst gave a 3:1 cis/trans mixture.

TABLE II

Comparison of Oxidation Reaction with Various Metal Catalysts

| CATALYST (MOLE %) | REACTION COMPONENTS AFTER 3 Hours (% by gc) | | | | | |
|---|---|---|---|---|---|---|
| | I. | II. | III. | IV. | V. | OTHER |
| Mo(CO)$_6$ (0.31) | 53 | 14.5 | 16 | 3.4 | 9 | 4 |
| Ti(i-PrO)$_4$ (1.0) | 2 | 8.6 | 28.7 | 39.5 | 21.4 | some |
| VO(acac)$_2$ (0.25) | 6.4 | 6 | 9.6 | 6 | 72 | none |

I: Cyclopentene
II: Epoxycyclopentane
III: 2-cyclopenten-1-ol
IV: 2-cyclopenten-1-one
V: 2,3-epoxycyclopentan-1-ol The second aspect of this invention is a process for synthesizing 7-oxa-11-deoxy prostaglandin analogues comprising the steps of
(a) reacting protected cis-2,3-epoxycyclopentan-1-ol with an alkynylalane reagent;
(b) reacting the product of step (a) with an ester of an omega-iodo alkanoic acid, containing from 3 to 12 carbon atoms.

The synthesis of prostaglandin analogues from all cis 1,2-epoxycyclopentane-3,5-diol has been disclosed by Fried, et al., Ann. NY Acad. Sci., 180 (1971) 38, and is incorporated herein by reference. The key step in this synthesis is the attachment of the substituent in the beta-position by reaction of the protected epoxy diol with an alkynylalane reagent.

Reaction of cis 2,3-epoxycyclopentan-1-ol with an alkynylalane reagent would be expected to result in a mixture of 2-trans substituted and 3-trans substituted products, of which only the 3-trans substituted one is suitable for further synthesis. It has now surprisingly been found that the alkynylalane reaction yields almost exclusively the desired 3-substituted product. The regio-selectivity of this substitution contributes importantly to the suitability of cis-2,3-epoxycyclopentan-1-ol for the synthesis of prostaglandin analogues. The present invention thus provides a total synthesis for a novel class of prostaglandin analogues, starting from the relatively inexpensive cyclopentene.

Cyclopentene (VII) is oxidized with singlet oxygen to cis-2,3-epoxycyclopentan-1-ol (VI) in the manner described above. Then, the hydroxyl group is protected with a suitable protecting group, e.g. methoxymethyl. The protected cyclopentane compound is reacted with the alkynylalane reagent.

The alkynylalane reagent is formed in situ by reaction of dimethylaluminum chloride with a lithiated 1-alkyne. Any 1-alkyne is suitable for the purpose of the present invention. Preferred 1-alkynes are 1-hexyne and 1-octyne, and derivatives thereof. The most preferred are the 1-octynes. The 1-octyne may have substituents at the 3 and/or 4 positions. Examples of substituted 1-octynes suitable for use in prostanoid synthesis are (R,S)-1-octyn 3-ol, (R)-1-octyn-3-ol, (S)-1-octyn-3-ol, 3-methyl (S)-1-octyn-3-ol, 4-methyl(R,S)-1-octyn-3-ol, 4-methyl(R)-1-octyn-3-ol, 4-methyl(S)-1-octyn-3-ol, 4,4 dimethyl(R,S)-1-octyn-3-ol, 4,4 dimethyl-(R)-1-octyn-3-ol, 4,4 dimethyl-(S)-1-octyn-3-ol, (R,S)-1-octyn-4-ol, (R)-1-octyn-4-ol, (S)-1-octyn-4-ol and 4-methyl-1-octyn-4-ol.

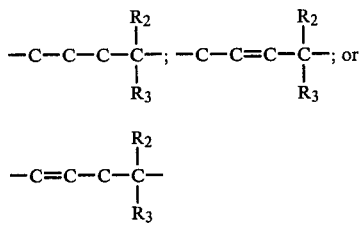

and $R_2$ and $R_3$ are each H, $CH_3$, $C_2H_5$ or $C_3H_7$.

The omega-iodo derivatives of hexanoic acid and 4-hexenoic acid are preferred herein. Most preferred is the hexanoic acid derivative.

The hydroxyl groups in (IX) are deprotected by acid catalyzed de-etherification. Thus, reaction with trifluoroacetic acid (TFA) followed by reaction with $BF_3$ etherate gives methyl-9-alpha-hydroxy-15-hydroxy-7-

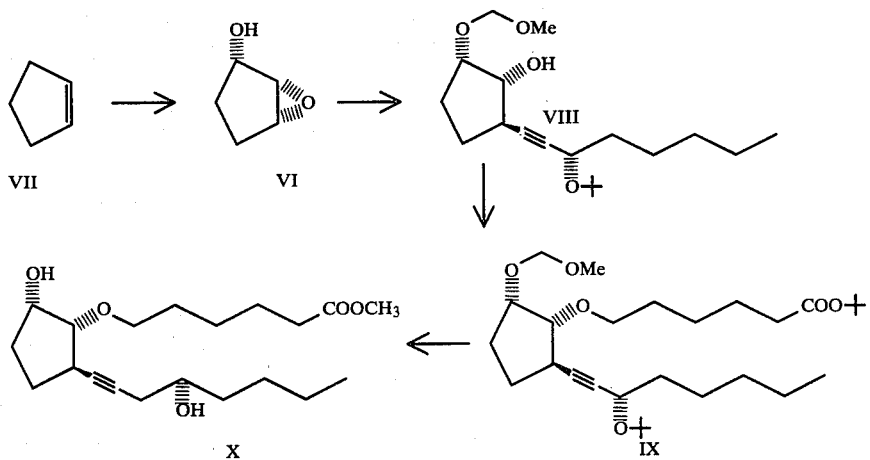

Highly preferred alkynylalane reagents herein are those derived from 1-octyne, (R,S)-1-octyn-3-ol; (S)-1-octyn-3-ol, and 3-methyl (S)-1-octyn-3-ol. Most highly preferred are the alkynylalane reagents derived from (R,S)-1-octyn-3-ol and (S)-1-octyn-3-ol.

In case the 1-octyne contains an alcoholic hydroxyl group, this group has to be protected prior to the reaction with dimethylaluminum chloride, by e.g. reaction to an ether in a manner similar to the protection reaction for the alcoholic hydroxyl in compound I. The t-butyl ether generally is a suitable protective group for the 1-octynol hydroxyl group.

The alkynylalane reagent thus formed is reacted with compound (VI) to give the corresponding 3 beta-octynyl-alpha-1-methoxymethoxy alpha cyclopentan-2-ol (VIII). Compound (VIII) is reacted to compound (IX) by a Williamson synthesis. The carboxylic hydroxyl group needs to be protected prior to the exposure of the molecule to sodium hydride. The t-butyl ester is a suitable protecting group. Any omega-iodo substituted carboxylic acid is suitable for this reaction. Preferred carboxylic acids are carboxylic acids containing from 3 to 12 carbon atoms. Particularly suitable are the omega-iodo alkanoic acid derivatives of the formula:

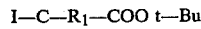

wherein $R_1$ is oxa-prost-13,14-ynoate (X), which is a member of the novel class of prostanoids of this invention. Other members of this class can be derived herefrom by:
  reacting one or more of the hydroxy groups of the prostaglandin analogue with chromium trioxide;
  reacting the prostaglandin analogues with hydrogen in the presence of a Lindlar catalyst;
  reacting the prostaglandin analogue with hydrogen in the presence of a coal-supported palladium catalyst;
  reacting the prostaglandin analogue with diphenyl disulphide, followed by irradiation with u.v. light.
or by any combination of these steps.

Thus, hydrogenation of (X) over a Lindlar catalyst gives methyl-9-alpha-hydroxy-15-hydroxy-7-oxa-cis-prost-13,14-enoate (XI). The latter compound can be oxidized in a Collins reaction to methyl-9,15-dioxo-7-oxa-cis-prost-13,14-enoate (XII).

Details of the synthesis of 7-oxa-prostaglandin in accordance with the process of the present invention will become apparent from the following examples.

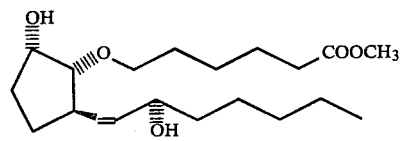

XI

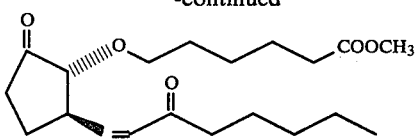

EXAMPLE IV 2,3-Epoxymethoxymethoxycyclopentane (1) was prepared in accordance with the invention as follows.

A dried flask with a magnetic stirring bar was charged with 180 ml freshly distilled THF and cooled to 0°–5° C. under argon. Potassium hydride (10 ml of a 22% dispersion in mineral oil) was then added, followed by 4.6 g (46 mmol) 2,3-epoxycyclopentan-1-ol as a solution in 12 ml THF, dropwise with stirring. After stirring 5–10 min. more, 8.9 g iodomethyl methyl ether was added, slowly with stirring. After 15 min., the reaction was quenched by careful, slow addition of 45 ml 1N NaHCO₃. After removing the THF under vacuum, 100 ml H₂O was added and the reaction mixture was extracted with three 75 ml portions of CH₂Cl₂. The combined organic portions were filtered and concentrated under vacuum to give the crude product. This material was purified by fractional distillation to give 4.15 g pure product (bp 44°–5° C. at 0.15 mm), a 63% yield.

¹H NMR (60 MHz): delta 4.65(s,2H) 4.1(m,1H), 3.55–3.3(m,2H), 3.35(s,3H), 2.45–1.15(m,4H).

¹³C NMR (20 MHz): 96.19, 78.69, 57.08, 55.26, 55.10, 25.42, 24.07 ppm.

EXAMPLE V

2-Alpha-hydroxy-1-alpha-methoxymethoxy-3-beta-(3-t-butoxy-1-octyn yl)-cyclopentane (2) was prepared from compound (1) by reaction with n-butyllithium in the following manner.

To a solution of 3.16 g (17.36 mmol, 2.5 equiv.) 3-t-butoxy-1-octyne in 20 ml dry toluene at 0° C. under argon was added 10.85 ml n-butyllithium (1.6 M, 2.5 equiv.). After stirring 15 min, 6.8 ml dimethylaluminum chloride (2 M, 2 equiv.) was added, dropwise via syringe. After 50 min. more, 1 g epoxide (1) (6.94 mmol) was added dropwise, as a solution in 5 ml toluene. The cooling bath was removed, and the stirring was continued for 4 hrs. The reaction was then quenched by careful addition of saturated aqueous Na₂SO₄, and the mixture was partitioned between 200 ml H₂O and 100 ml ether. The aqueous layer was extracted twice more with 150 ml portions of ether, then the combined ethereal portions were dried (molecular sieves), filtered, and concentrated under vacuum to give the crude product, which was purified by flash chromatography with 4:1 hexane:ethyl acetate to give 1.66 g pure adduct (73% yield).

IR (Neat): 3480, 2200(w) cm⁻¹

¹H NMR (60 MHz): delta 4.6(s,2H), 4.2–3.8(m,3H), 3.35(s,3H), 1.25(s,9H)

¹³C NMR (22.5 MHz): 96.15(O—CH₂—O); 85.38, 84.40(13,14); 79.18, 78.33(C8,9); 74.28(C—Me₃); 62.14(C15); 55.55(OMe); 37.86, 35.77(C12,16); 31.59(C18); 28.39(C—Me₃); 28.00, 27.81, 25.33(C10,11,17); 22.65(C19); 14.03(C20) ppm.

In the same manner epoxide 1 was reacted with 1-hexyne, 1-octyne, 3(S)t-butoxy-1-octyne, 3-(R)t-butoxy-1-octyne, 3-methyl-3(R,S)t-butoxy-1-octyne, 4,4-dimethyl-3(R,S)t-butoxy-1-octyne, and the corresponding 3-beta substituted 2-alpha hydroxy-1-alpha-methoxymethoxy cyclopentane compounds were secured.

Similar compounds are secured when epoxide 1 is reacted with 4-methyl-3-t-butoxy-1-oxtyne, 4-methyl-3(S)t-butoxy-1-octyne, 4-t-butoxy-1-octyne, 4(S)t-butoxy-1-octyne, and 3(S)t-butoxy-4(S)t-butoxy-1-octyne.

EXAMPLE VI

Compound (2) was reacted to t-butyl-9-alpha-methoxymethoxy-7-oxa-15-t-butoxy-prost-13,14-ynoate (3) by Williamson synthesis as follows:

A suspension of 0.44 g sodium hydride (50% dispersion in mineral oil, 3 equiv.) in 22 ml dry DMSO was heated in a 70° C. oil bath under argon for 50–60 min., at which time hydrogen evolution stopped. The solution was cooled to 20° C. (under argon) and a solution of 1 g alcohol (2) (3.06 mmol) in 3 ml DMSO was added dropwise via syringe. After 5 min. 4.57 g 6-iodo-t-butyl hexanoate (15.33 mmol, 5 equiv.) was added in a slow stream, via syringe. After stirring 3 hrs., this mixture was added to a separatory funnel containing 50 ml H₂O and 50 ml saturated aqueous NaCl. The mixture was extracted with 3 50 ml portions of ether; the organic layers were combined, dried (molecular sieves), filtered, and concentrated under vacuum to give the crude product. Upon purification by flash chromatography (4:1 hexane:ethyl acetate) two fractions were isolated: the first (R_f>0.5 with 3:1 hexane:ethyl acetate) was product 3, 0.85 g (56% yield); the second was recovered alcohol (2), 0.43 g (43%).

IR (Neat): 1730(s) cm⁻¹

¹H NMR (60 MHz): delta 4.6(s,2H), 4.2–3.85(m,2H), 3.7–3.3(m,3H), 3.25(s,3H), 2.9–2.55(m-1H), 1.4(s,9H), 1.2(s,9H)

¹³C NMR (22.5 MHz): 172.98, 95.63, 86.56, 86.36, 83.88, 79.83, 76.64, 74.22, 70.37, 62.14, 55.29, 37.86, 35.51, 32.90, 31.59, 29.70, 28.39(3C), 28.13(3C), 27.94, 27.74, 25.72, 25.34, 25.00, 22.58, 14.03 ppm.

In the same manner alcohol (2) is reacted with t-butyl-6-iodo-3-hexenoate, t-butyl-6-iodo-4-hexenoate, t-butyl-6-iodo-2,2 dimethyl-hexanoate, t-butyl 6-iodo-2,2 diethyl-hexanoate, t-butyl-6-iodo-2 methoxymethoxy-hexanoate, and the corresponding prost-13,14-ynoates are obtained.

EXAMPLE VII methyl-9-alpha-hydroxy-15-hydroxy-7-oxa-Prost-13,14-ynoate (4) was obtained from (3) by removal of the protecting groups:

To a solution of 1.85 g (3.73 mmol) 3 in 8 ml CH₂Cl₂, stirred at −10° C. under argon, was added 8 ml trifluoroacetic acid (which had been cooled to 0° C.) in one portion. After 10 min. the cooling bath was removed and the reaction was stirred 60–90 min. longer. A vacuum pump was attached, and all volatiles were thus removed. The brown residue was taken up in 75 ml methanol (anhydrous), and 7.5 ml BF₃ etherate was added; this mixture was refluxed 10 min on a steam cone, and then concentrated under vacuum to remove most of the methanol. The remainder was partitioned between 100 ml NaHCO₃ and 75 ml CH₂Cl₂. After extracting the aqueous layer twice more, the organic layers were combined, filtered, and concentrated under vacuum to give the crude product. Purification by flash chromatography with 1.2:1 hexane:ethyl acetate gave 1.16 g pure prostanoid (88% yield).

IR (Neat): 3480, 2250(w), 1745(s)

$^1$H NMR (60 MHz): delta 4.5–4.0(m,2H), 3.9–3.5(m,3H), 3.65(s,3H)

$^{13}$C NMR (22.5 MHz): 174.09(C1); 87.01(C8); 82.84(C14); 77.03(C13); 71.54, 70.30(C9,6); 62.40(C15); 51.50(—O—CH$_3$); 38.12(C12); 33.88, 32.96, 31.53, 30.09, 29.44, 28.26, 25.65, 24.93, 24.61, 22.58, 13.97(CH$_2$CH$_3$) ppm.

Compound (4) belongs to the novel class of 7-oxa-prostanoic acid derivatives of this invention. The keto-analogues of (4) can be prepared therefrom by oxidation with chromium trioxide (Example VIII). If the 15-hydroxy is protected with TFA prior to the reaction with chromium trioxide (Example IX), the 9-hydroxy is oxidized selectively (Example X).

EXAMPLE VIII

Compound (4) was converted to methyl-9,15-dioxo-7-oxa-prost-13,14-ynoate (5) by oxidation with chromium trioxide as follows.

A mixture of 2.56 g chromium trioxide, 4.13 ml dry pyridine, and 65 ml CH$_2$Cl$_2$ was stirred 15 min. at room temperature. A solution of 500 mg diol (4) (1.41 mmol) in 2 ml CH$_2$Cl$_2$ was added via pipette, and the resulting heterogeneous mixture was stirred another 15–20 min. After adding 100 ml ether, the mixture was filtered through a short silica gel column to remove the chromium salts (the column was then washed with 100 ml ethyl acetate). The combined effluent was concentrated under vacuum, and the residue was purified by flash chromatography with 3:1 hexane ethyl acetate to get 440 mg pure diketone (89% yield).

IR (Neat): 2230(s), 1760(s), 1730(s), 1680(s) cm$^{-1}$ $^1$H NMR (60 MHz): delta 3.85–3.45(m,3H), 3.61(s,3H)

$^{13}$C NMR (22.5 MHz): 211.82(C9); 187.40(C15); 173.64(C1); 91.84(C13); 84.99(C8); 81.92(C14); 71.35(C6); 51.11(O—CH$_3$); 45.24(C12); 34.14, 33.68(2C), 30.88, 29.18, 25.26, 24.41, 23.76, 23.50, 22.13, 13.64(CH$_2$CH$_3$) ppm.

EXAMPLE IX

Compound (4) was reacted with TFA to form methyl-9-alpha-hydroxy-7-oxa-15-trifluoroacetoxy-prost-13,14-ynoate (6) in the following manner:

To a solution of 0.1988 g diol (4) in 8 ml CH$_2$Cl$_2$, stirred at −78° C. under argon, was added 0.064 ml dry pyridine (1.5 equiv.), then 0.083 ml trifluoroacetic anhydride (1.05 equiv.), slowly via syringe. After stirring 2 hrs, the reaction mixture was concentrated under vacuum and purified by flash chromatography; 2:1 hexane:ethyl acetate eluted a diacetate fraction (R$_f$=0.70, 0.103 g 34% yield), and a monoacetate fraction (R$_f$=0.41, 0.0855 g, 34% yield); 1:1 hexane:ethyl acetate eluted recovered starting material (R$_f$=0.17 with 2:1 hexane:ethyl acetate, 0.056 g, 28% yield). Starting material was regenerated from the diacetate fraction by stirring the latter in 2:1 MeOH:IN NaHCO$_3$ for 1–2 hrs. Spectral analysis showed that the monoacetate fraction consisted of one, pure isomer (the title compound).

IR (Neat): 3450, 2220(w), 1785, 1740(br) cm$^{-1}$ $^1$H NMR (60 MHz): delta 5.5–5.1(m,1H), 4.3–3.9(m,2H), 3.7–3.3(m,3H), 3.6(s,3H)

$^{13}$C NMR (22.5 MHz): 174.02(C1); 90.93(C14); 87.01(C8); 76.50(C13); 71.54, 70.56, 69.32(C6,9,15); 51.50(O—CH$_3$); 34.60, 33.94, 32.90, 31.14, 30.03, 29.50, 28.00, 25.65, 24.67, 24.48, 22.45, 13.90 ppm. (Diacetate)

IR (Neat): 2250(w), 1785(s), 1740(br) cm$^{-1}$ $^1$H NMR (60 MHz): delta 5.5–5.1(m,2H), 4.4—3.3(m,3H), 3.6(s,3H)

EXAMPLE X

Compound (6) was selectively oxidized at the 9 position; then the hydroxyl group at the 15 position was deprotected and methyl 15-hydroxy-7-oxa-9-oxo-prost-13,14-ynoate (7) was isolated. The reaction scheme was as follows:

A solution of chromium trioxide (0.18 g), pyridine (0.28 ml), and CH$_2$Cl$_2$ (3.9 ml) was stirred at room temperature for 15 min. A solution of monoacetate (6) (0.0855 g, 0.19 mmol) in 1 ml CH$_2$Cl$_2$ was added in one portion, and the stirring was continued for 15 min. Ether (10 ml) was added, and the mixture was passed through a short silica gel column. The effluent was concentrated under vacuum, then dissolved in 5 ml methanol; 2 ml IN NaHCO$_3$ was added, with stirring. After 45 min., the mixture was transferred to a separatory funnel with 100 ml H$_2$O, and extracted with three 50 ml portions of ethyl acetate. The organic layers were combined, dried (molecular sieves), filtered, and concentrated to give the crude product, purified by flash chromatography (1:1 hexane:ethyl acetate) to give keto alcohol (7) (0.0603 g, 90% yield).

IR (Neat): 3450, 2190(w), 1730(br) cm$^{-1}$ $^1$H NMR (60 MHz): delta 4.5–4.15(m,1H)4.2–3.4(m,3H), 3.6(s,3H)

$^{13}$C NMR(22.5 MHz): 213.59(C9); 174.35(C1); 85.90(C8); 84.53, 84.21(C13,14); 71.28(C6); 62.47(C15); 51.57(O—CH$_3$); 37.99, 34.47, 34.01(2C), 31.53, 29.37, 25.52, 24.93, 24.67, 22.65, 14.03 ppm.

EXAMPLE XI

By varying the 1-alkyne reagent in the reaction of Example V, different prostanoid precursors could be synthesized. Thus, 2-alpha-hydroxy-1-alpha-methoxymethoxy-3-beta-(3 -dimethyl-t-butyl silyloxy)-1-octynylcyclopentane (8) was prepared from epoxy ether (1) by reaction with an alane reagent derived from 3-(dimethyl-t-butyl silyloxy)-1-octyne, exactly following the experimental procedure previously described for the synthesis of compound (2) (Example V). Thus, 1.26 g(8.75 mmole) epoxide (1), upon treatment with 2 equivalents of the above, gave a crude product (R$_f$0.37 using 3:1 hexane:ethyl acetate on silica gel), which was purified by flash chromatography with 4.5:1 hexane:ethyl acetate to give 1.45 g pure product (43% yield).

IR (Neat): 3490, 1460, 2220, 1250, 835 cm$^{-1}$ $^1$H NMR(60 MHz): delta 4.6 (s, 2H) 3.7–4.3(m,3H), 3.3(S,3H), 1.8(s,9H), 0.1(s,6H)

$^{13}$C NMR (22.5 MHz): 96.09, 85.45, 83.62, 79.12, 78.27, 63.12, 55.55, 38.84, 35.58, 31.40, 27.94, 27.68, 25.78, 25.00, 22.52, 18.21, 13.97, 4.44, 4.96 ppm.

EXAMPLE XII

By the Williamson synthesis of Example VI, Compound (8) was converted to t-butyl 9-alpha-methoxymethoxy-7-oxa-15-dimethyl-t-butyl-silyloxy-prost-13,14-ynoate (9).

The latter compound was prepared from alcohol (8) by a Williamson ether synthesis exactly as described for compound (3) (Example VI). From 1.7 g (4.42 mmol) of alcohol (8) was obtained 1.14 g of 9 (46% yield) and 0.85 g recovered (8) (50% recovery); the R$_f$ values on silica gel using 5:1 hexane:ethyl acetate were 0.46 and 0.31, respectively. The separation was effected by flash chromatography with 7:1 hexane:ethyl acetate.

IR (Neat): 1730 cm$^{-1}$ $^1$H NMR (60 MHz): delta 4.5(s,2H), 3.8–4.35(m,2H), 3.2–3.75(m,3H), 3.2(s,3H), 2.7(m,1H), 1.35(s,9H), 0.8(s,9H), 0.05(s,6H)

$^{13}$C NMR (22.5 MHz): 172.59(C1); 95.38(O—CH$_2$—O); 86.36(C8,C13); 82.90(C14); 79.44(O—C Me$_3$); 76.18(C9); 70.17(C7); 62.99(C15); 55.03 (OCH$_3$); 38.71, 35.25, 32.57, 31.27, 29.44, 27.87(3C), 27.55, 25.65(3–4C), 24.74, 22.39, 18.02, 13.77, 4.57, 5.09 ppm

EXAMPLE XIII

Due to the choice of the protection group of the hydroxyl at the 15 position, this hydroxyl was deprotected selectively to give t-butyl-15-hydroxy-9-alpha-methoxymethoxy-7-oxa-prost-13,14-ynoate (b 10), as follows:

410 mg (0.74 mmol) silyl ether (9) was dissolved in 4.4 ml dry THF and cooled to 0° C. under argon. Tetrabutylammonium fluoride (IM in THF, 1.48 ml, 2 equiv.) was added dropwise via syringe. After 5 min. the solution was allowed to warm up to 25° C., and stirring was continued for 40 min. The reaction mixture was then added to a separatory funnel with 100 ml IN NaHCO$_3$, and was extracted with 3 40 ml portions of ethyl acetate. The organic layers were combined, dried (molecular sieves), filtered, and concentrated under vacuum. This crude extract was purified by flash chromatography (3:1 hexane:ethyl acetate) to give 335 mg pure alcohol (100% yield).

$^1$H NMR (60 MHz): delta 4.6(s,2H), 3.8–4.5(m,2H), 3.3–3.7(m,3H), 3.25(s,3H), 2.5–3.0(m,2H), 1.4(s,9H).

$^{13}$C NMR (22.5 MHz): 173.18(C1); 95.56(O—CH$_2$—O); 87.21(C13); 86.69(C8); 82.77(C14); 79.96(O—C Me$_3$); 76.37(C9); 70.37(C7); 62.40(C15); 55.29(OCH$_3$); 38.19, 35.51, 32.77, 31.59, 29.57, 28.13(3C), 27.94, 27.81, 25.65, 24.94, 22.65, 14.03 ppm

EXAMPLE XIV

After the selective deprotection of the hydroxyl at the 15 position, (10) was oxidized to the ketone t-butyl 9-alpha-methoxymethoxy-7-oxa-15-oxo-prost-13,14-ynoate (11).

A solution of 0.67 g CrO$_3$, 1.07 ml pyridine, and 17 ml CH$_2$Cl$_2$ was stirred 15 min. at 25° C. A solution of 17 ml CH$_2$Cl$_2$ was added, and the resulting mixture was stirred 15 min. more. After adding 100 ml Et$_2$O, the mixture was filtered through a short silica gel column, starting with 50 ml ethyl acetate. The combined effluent was concentrated under vacuum, and purified by prep tlc (4×500μ, 20×20 cm silica gel plates with 4:1 hexane:ethyl acetate) to give 260 mg pure ketone (80% yield).

IR (Neat): 2200(s), 1725(s); 1670(s) cm$^{-1}$ $^1$H NMR (60 MHz): delta 4.6(s,2H), 4.1(m,1H), 3.4–3.9(m,3H), 3.3(s,3H), 1.4(s,9H)

$^{13}$C NMR (22.5 MHz): 188.06(C15); 172.85(C1); 95.83(C13); 95.56(O—CH$_2$—O); 86.43(C8); 81.40(C14); 79.83(O—C Me$_3$); 76.05(C9); 70.63(C7); 55.35(OCH$_3$); 45.50, 35.44; 32.83, 31.14, 29.57, 28.07(3–4C), 27.15, 25.59, 24.87, 23.83, 22.39, 13.84 ppm

EXAMPLE XV

Compound (11) was converted to methyl 9-alpha-hydroxy-7-oxa-15-oxo-prost-13,14-ynoate (12) as follows.

Ketone (11) (220 mg, 0.5 mmol) was dissolved in 1.4 ml CH$_2$Cl$_2$ and cooled to −15° C. under argon; trifluoroacetic acid (1.4 ml, cooled to 0° C.) was added, with stirring. After 10 min. the cooling bath was removed, and the reaction stirred for 90 min. more. The reaction mixture was concentrated under vacuum and passed through a silica gel column (elution with 94:3:3 CHCl$_3$:methanol:acetic acid). The 147 mg crude acid thus obtained was esterified with CH$_2$N$_2$ by the usual method to give crude methyl ester, which was purified by preparative tlc (3×500μ silica gel plates, developed with 1.8:1 hexane:ethyl acetate) to give 90 mg pure ester (65% overall yield).

$^1$H NMR (60 MHz): delta 4.0–4.3(m,1H), 3.5–3.9(m,3H), 3.7(s,3H), 2.8–3.1(m,1H)

$^{13}$C NMR (22.5 MHz): 188.12(C15); 173.90(C1); 95.63(C13); 86.88(C8); 81.53(C14); 71.48, 70.63(C7,9); 51.44(OCH$_3$); 45.50, 33.88, 32.96, 31.14, 29.90, 29.44, 27.68, 25.59, 24.61, 23.83, 22.39, 13.84 ppm

EXAMPLE XVI

The prostynoate prepared according to example VII (Compound (4)) was hydrogenated to the corresponding cis prostenoate, methyl 9-alpha-hydroxy-15-hydroxy-7-oxa-cis-prost-13,14-enoate (13), as follows.

A solution of 410 mg (1.16 mmol) diol (4) in 20 ml absolute ethanol was hydrogenated over 50 mg Lindlar catalyst at 760 mm. After 1 equivalent of hydrogen was consumed, the mixture was filtered, concentrated, and purified (flash chromatography, 1:1 hexane:ethyl acetate) to give 410 mg cis-olefin (99% yield). Spectral data (below) indicate a 1:1 mixture of diastereomers.

$^1$H NMR (90 MHz): delta 5.1–5.9(m,2H), 3.7(s,3H)

$^{13}$C NMR (22.5 MHz): 173.96, 135.78, 134.73, 134.34, 133.36(C13,14); 87.60, 87.21(C8); 70.69, 70.43, 70.30, 69.91, 67.95, 66.45(C7,9,15); 51.44(O—CH$_3$); 40.21, 39.88, 37.79, 36.75, 33.88, 32.05, 31.92, 30.16, 29.83, 29.63, 29.18, 27.68, 26.96, 25.65, 25.46, 25.26, 25.13, 24.67, 24.54, 22.65, 14.03 ppm In the same manner, compound (7) (Example X) was converted to the corresponding keto prostenoate: methyl-15-hydroxy-7-oxa-9-oxo-cis-prost-13-14-enoate (14).

EXAMPLE XVII

The 9,15-dihydroxy prostynoate of Example VII (Compound (4)) was hydrogenated to the corresponding prostanoate (15); (15) was subsequently oxidized to the 9,15 dioxo analogue (16).

A solution of 305 mg (0.86 mmol) diol (4) in 25 ml abs. ethanol was hydrogenated over 30 mg catalyst (50% Pd/C) at 760 mm. After 2 equivalents of hydrogen uptake, the mixture was filtered and concentrated under vacuum to give crude olefin, which could be purified (flash chromatography using 1:1 hexane:ethyl acetate) or used directly in the next step.

A mixture of 1.54 g chromium trioxide, 2.48 ml pyridine, and 35 ml methylene chloride was stirred 15 min. at 25° C. The crude diol (15) was added as a solution in 2 ml methylene chloride. After 15 min., the crude diketone was isolated by the usual method and purified by flash chromatography (25:1 hexane:ethyl acetate) to give 250 mg pure diketone (82% overall yield).

For Diol (15):

$^{13}$C NMR (22.5 MHz): 174.02, 87.60, 71.93, 71.74, 70.83, 69.91, 51.44, 41.32, 41.06, 37.60, 37.40, 35.77, 33.88, 31.92, 30.35, 29.57, 26.57, 26.37, 25.72, 25.33, 24.61, 22.58, 13.97 ppm For Diketone (16):

$^{13}$C NMR (22.5 MHz): 216.58(C15); 210.26(C9); 173.70(C1); 87.08(C8); 70.56(C6); 51.18(OCH$_3$); 42.56, 41.19, 39.95, 34.79, 33.75, 31.20, 29.50, 27.55, 25.46, 24.54, 23.30(2C); 22.26, 13.71 ppm

EXAMPLE XVIII

Compound (14) (Example XVI) was converted to the trans isomer methyl-15-hydroxy-7-oxa-9-oxo-trans-prost-13,14-enoate (17) as described below. This cis-trans isomerization reaction is described in more detail by C-Moussebois and J. Dale, *J. Chem. Soc.*, 206 (1966), incorporated herein by reference.

To a solution of 58 mg keto alcohol (14) (0.16 mmol, isomer "T") in 4.5 ml cyclohexane was added 36 mg diphenyl disulfide. After purging with argon, the stirred solution was irradiated (350 nm) for 90 min. using a Rayonet photochemical reactor. The reaction mixture was then concentrated and purified by flash chromatography (using 1:1 hexane:ethyl acetate) to give some recovered starting material (ca. 25mg, impure) and product (14.5mg, 25% yield) with R$_f$ values of 0.52 and 0.28, respectively (silica gel, 1:1 hexane:ethyl acetate).

IR (Neat): 3490, 1740(br), 970(m) cm$^{-1}$ $^1$H NMR (60 MHz): delta 5.3–6.0(m,2H), 3.7(s,3H), 3.5(d,1H; J-11 Hz)

$^{13}$C NMR (22.5 MHz): 215.74, 174.22, 134.92, 131.14, 86.43, 72.65, 71.09, 51.50, 44.98, 37.40, 34.79, 34.01, 31.79, 29.57, 25.59, 25.13, 24.74, 23.63, 22.65, 14.03 ppm

EXAMPLE XIX

By its nature, the synthesis described in Example IV through XVIII produces racemic mixtures of the 7-oxa prostanoic acid derivatives. Optically pure compounds were prepared as follows.

dl-1-Octyn-3-ol was resolved to (S)-1-octyn-3-ol using 1(−)-alpha-methyl benzylamine. (S)-1-Octyn-3-ol was used in the synthesis of methyl-(S)-15-hydroxy-7-oxa-9-oxo-prost-13,14-ynoate (18) in the manner described in Examples V through VII and IX-X. Similarly, methyl-(R)-15-hydroxy-7-oxa-9-oxo-prost-13,14-ynoate (19) was prepared from R-1-octyn-3-ol,

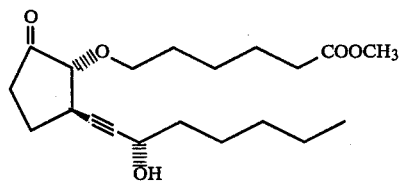
(18)

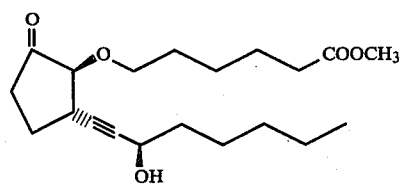
(19)

compounds (18) and (19) were separated from their diastereomers by repeated recrystallization. The specific rotation of compound (18) was determined to be +41.97° in diethyl ether. That of compound (19) was −40.42°.

Via oxidation of the hydroxyl group (c.f. example VIII) the corresponding 15-oxo-prostynoates were prepared (compounds (20) and (21))

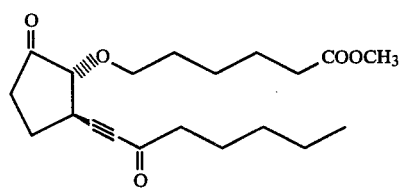
(20)

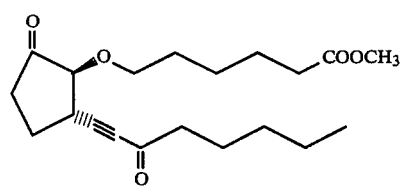
(21)

The specific rotations were +56.12° and −52.12°, respectively.

Another aspect of this invention are the 7-oxa-11-deoxy prostaglandin analogues of the formula

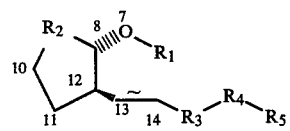

wherein the C$_{13}$–C$_{14}$ bond is a single bond, cis double bond, or trans double bond, or triple bond; R$_1$ is

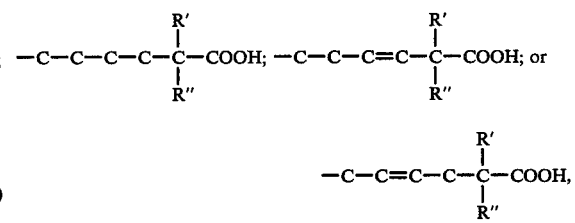

R' and R" are each H, CH$_3$, C$_2$H$_5$ or C$_3$H$_7$;

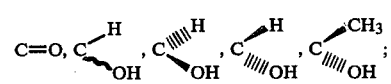

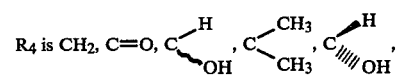

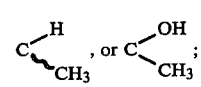

and esters and salts thereof.

Preferred herein are the compounds wherein R$_5$ is C$_4$H$_9$. The substituent R$_1$ is preferably

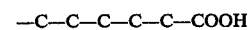

The C$_{13}$–C$_{14}$ bond is preferably a double bond or a triple bond, more preferably a triple bond.

Preferred also are compounds wherein R$_3$ is

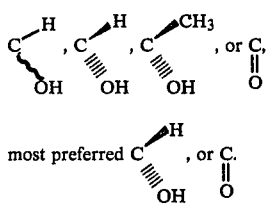

$R_4$ is preferably $CH_2$,

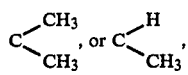

most preferably $CH_2$.

A number of the 7-oxa prostanoic acid derivatives has been tested for cytoprotective activity in rats. In this test, Sprague-Dawley rats are fasted for 24 hours prior to the pretreatment. The pretreatment is oral administration of a 5 mg per kg body weight dose of the prostanoid in 2.5 ml of a vehicle consisting of Tween 80 (0.75%) and the balance water. The control animals are given 2.5 ml of the vehicle, without prostanoid. A half hour after the pretreatment, absolute ethanol is administered orally to the animals, in a dose of 10 ml per kg body weight. One hour later the animals are sacrificed, their stomachs dissected out, opened along the greater curvature and the mucose examined for lesions. The average lesion length is expressed as percentage of the average lesion length found in the stomach mucosa of control animals.

Importantly, this test measures the active cytoprotective properties of the prostanoids, independent of the gastric secretion inhibition that these compounds may or may not show. The test is discussed more fully by Robert et al., Gastroenterology 77 (1979) 433, incorporated herein by reference.

EXAMPLE XX methyl-7-oxa-9-oxo-Prostanoate derivatives were tested for cytoprotective properties. The compounds differed with respect to the nature of the $C_{13}$–$C_{14}$ bond (triple, cis or trans double, or single), the substituent(s) at the 15-position and at the 16-position. The following results were obtained.

TABLE I

Cytoprotective properties of 7-oxa-9-oxo-methyl prostanoate derivatives having different substituents at the 15 and 16 positions.

| COMPOUND | | | LESIONS | |
|---|---|---|---|---|
| $C_{13}$–$C_{14}$ | 15-subst. | 16-subst. | % control | % reduction |
| triple | (R,S)OH | H,H | 31 | 69 |
| cis | (R,S)OH | H,H | 31 | 69 |
| triple | oxo | H,H | 4 | 96 |
| cis | oxo | H,H | 113 | −13 |
| trans | oxo | H,H | 118 | −18 |
| single | oxo | H,H | 128 | −28 |
| triple | (S)OH | H,H | 4 | 96 |
| triple | (R,S)OH,Me | H,H | 82 | 18 |
| cis | (R,S)OH,Me | H,H | 71 | 29 |
| trans | (R,S)OH,Me | H,H | 54 | 46 |
| single | (R,S)OH,Me | H,H | 67 | 33 |
| triple | H,H | H,H | 81 | 19 |
| triple | oxo | Me,Me | 16 | 84 |

The results indicate that for optimum cytoprotective properties it is highly desirable that the substituent at the 15-position be either oxo or (S)OH. If the substituent is oxo, the $C_{13}$–$C_{14}$ bond preferably is a triple bond.

EXAMPLE XXI

A number of methyl-7-oxa-9-alpha-hydroxy prost-13,14-ynoate derivatives was tested for cycloprotective properties. The results are presented in Table II.

TABLE II

| COMPOUND | | | LESIONS | |
|---|---|---|---|---|
| $C_{13}$–$C_{14}$ | 15-subst. | 16-subst. | % control | % reduction |
| triple | H,H | H,H | 90 | 10 |
| triple | (R,S)OH | H,H | 93 | 7 |
| triple | (R,S)OH | Me,Me | 83 | 17 |
| triple | (S)OH | H,H | 45 | 55 |
| triple | (R)OH | H,H | 101 | −1 |
| triple | oxo | H,H | 20 | 80 |
| triple | oxo | H,H | 7[1] | 93[1] |

[1] Acid rather than methyl ester.

As in the previous example, oxo and S(OH) appear to be the preferred substituents at the 15-position.

EXAMPLE XXII

The optically pure compounds of Example XIX were tested for cytoprotective activity. The following results were obtained (Table III).

TABLE III

| Compound | Number | % Protection |
|---|---|---|
| (structure) | (18) | 96 |
| (structure) | (19) | −34 |
| (structure) | (20) | 96 |
| (structure) | (21) | 96 |

The activity of the enantiomers (20) and (21) was the same (and was the same also for the racemate, Table I, line 3). This suggests that the activity is independent of the stereochemistry at the positions 8 and 12 of the 9-oxo compounds. The striking difference between the activities of (18) and (19) must then be due to the C-15 stereochemistry. The absolute configurations of the compounds were not established. In view of the high cytoprotective activity it is assumed that compound (18) has the configuration as indicated, since this is the natural configuration.

What is claimed is:

1. A process for converting olefins to the corresponding alpha-epoxy alcohols comprising reacting an olefin with singlet oxygen in the 1 $\Delta$g state and converting the reaction product to an alpha-epoxy alcohol by in situ rearrangement in the presence of a catalytic amount of a heterogeneous or homogeneous catalyst containing a transition metal of group IVB, VB or VIB of the Periodic Table, excluding chromium.

2. A process according to claim 1 wherein the olefin is a mono-olefin, and the catalyst is a homogeneous catalyst.

3. A process according to claim 2 wherein the reaction mixture contains from about 5% to about 98% of an organic solvent which is miscible with the olefin.

4. A process for converting mono-olefins to the corresponding alpha-epoxy alcohols, whereby a reaction mixture comprising: a mono-olefin, from about 5% to about 98% of an organic solvent which is miscible with said mono-olefin; a catalytic amount of a soluble salt or metallo-organic complex of vanadium or molybdenum; and a catalytic amount of a photo-sensitizer; is purged with ground-state triplet oxygen and irradiated with visible light.

5. A process according to claim 4 wherein the catalyst is a vanadium catalyst, and the photo-sensitizer is selected from the group consisting of tetraphenyl porphin, methylene blue, erythrosin B, eosin, fluorescein, hematoporphin, rubene, rose bengal and the phthalocyanines and mixtures thereof.

6. A process according to claim 5 wherein the amount of catalyst is from about 0.1% to about 2.5%, and the amount of photosensitizer is from about 0.01% to about 2.5%.

7. A process for converting an olefin selected from the group consisting of cyclopentene, cis 9-octadecenoic acid and esters and salts thereof, cis 4-octene, 2,3-dimethyl-2-butene, alpha-pinene and beta-pinene, to the corresponding alpha-epoxy alcohol, whereby a reaction mixture comprising: the olefin, from about 80% to about 95% of a solvent selected from the group consisting of toluene and dichloromethane, from about 0.7% to about 1.3% vanadium acetylacetonate, from about 0.05% to about 1.3% tetraphenyl porphin; is purged with ground-state triplet oxygen and irradiated with visible light.

8. A process according to claim 7 wherein the olefin is cyclopentene and wherein the corresponding alpha-epoxy alchol is cis-2,3-epoxy cyclopentan-1-ol.

* * * * *